United States Patent [19]

Unruh et al.

[11] Patent Number: 5,616,785
[45] Date of Patent: Apr. 1, 1997

[54] SYNTHESIS OF AND HYDROFORMYLATION WITH FLUORO-SUBSTITUTED BIDENTATE PHOSPHINE LIGANDS

[75] Inventors: Jerry D. Unruh; Brigitte E. Segmuller; Gabriel R. Chapa, all of Corpus Christi; Kent E. Pryor, Houston, all of Tex.

[73] Assignee: Hoechst Celanese Corporation, Somerville, N.J.

[21] Appl. No.: 630,145

[22] Filed: Apr. 10, 1996

Related U.S. Application Data

[62] Division of Ser. No. 453,283, May 30, 1995, Pat. No. 5,567,856.
[51] Int. Cl.$^6$ .................. C07F 9/46; C07F 9/28
[52] U.S. Cl. .............................. 562/25; 568/13
[58] Field of Search .................. 562/25; 568/13

[56] References Cited

PUBLICATIONS

Kapoor et al., *J. Organomet. Chem.*, 276(2), pp.167–170 (1984).
Magnelli et al., *Inorg. Chem.*, 5(3), pp. 457–461 (1966).

*Primary Examiner*—Gary Geist
*Assistant Examiner*—Barbara S. Frazier
*Attorney, Agent, or Firm*—M. Susan Spiering; Donald R. Cassady

[57] ABSTRACT

Hydroformylation of alkenes to aldehydes in the presence of a rhodium complex catalyst is improved by the addition of a novel bidentate ligand of the formula

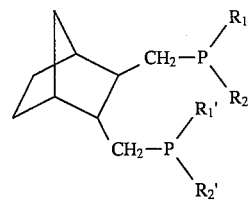

wherein $R_1$, $R_2$, $R_1'$ are organic radicals selected from alicyclic, aliphatic and aromatic groups of which at least one is preferably substituted with at least one electronegative moiety and the methylene groups are present at the trans-2,3 positions on the norbornane moiety. The invention also provides a novel method for producing the bidentate ligand and novel intermediate phosphine oxide and phosphinous acid compounds.

3 Claims, No Drawings

SYNTHESIS OF AND HYDROFORMYLATION WITH FLUORO-SUBSTITUTED BIDENTATE PHOSPHINE LIGANDS

This is a divisional of application Ser. No. 08/453,283 filed on 05/30/95, now U.S. Pat. No. 5,567,856.

FIELD OF THE INVENTION

The present invention is directed to novel phosphine ligands and, in particular, is concerned with novel bidentate phosphine ligands which are useful in the hydroformylation of olefins to aldehydes. The novel phosphine ligands of this invention have been found to improve the hydrofonnylation reaction rates.

Hydroformylation of an olefin to produce a formyl-substituted derivative of the olefin is now well-known in the an as an economically attractive method for producing, in particular, the aldehydes which are the primary intermediates in the manufacture of, for example, alkanols such as n-butanol and the corresponding alkanoic acids. Also important are such end products as 2-ethylhexanol, which is formed from n-butyraldehyde by a sequence of steps including aldol condensation, dehydration, and hydrogenation by methods which are well-established in the art.

While hydroformylation processes using cobalt carbonyl as the major component of the catalyst have been known and used for many years systems in which the catalyst comprises rhodium hydrido carbonyl complexed with an organic ligand have been developed more recently and are now favored over the older technology for several reasons including the fact that they can be used under relatively mild reaction conditions; and also the fact that the rhodium-catalyzed systems can be controlled so as to yield a product in which the normal isomer of the aldehyde predominates over the branched-chain isomer to a greater extent than has normally been obtained heretofore when using the older methods. It will be understood in this connection that for most industrial purposes, including use thereof as a raw material for production of the corresponding alkanolic acids (by catalytic oxidation of the aldehyde) and also for the production of higher molecular weight alcohol derivatives (as by aldol condensation, etc.), the normal aldehyde is strongly preferred over the branched-chain isomer. In the case of the butyraldehydes, for example, n-butyraldehyde finds a ready and expanding market whereas isobutyraldehyde has fewer uses and is considered an undesirable by-product. Similarly, in the case of longer-chain aldehydes such as heptanal, the normal isomers can be used to produce high-quality ester-type synthetic lubricants, while the properties of the corresponding branched-chain isomers are such that they have little value for such purposes.

Notwithstanding that the use of the rhodium-containing catalyst systems can result in the attainment of an improved linear:branched ratio (1:b ratio) in the aldehyde products as compared with the cobalt-based systems, formation of the branched-chain isomer continues to pose a significant economic drawback. Certain process conditions can also be used to influence the 1:b ratio. For example, by controlling such parameters as carbon monoxide partial pressure, carbon monoxide:hydrogen ratio, etc., it is possible to influence the product distribution somewhat in a favorable direction. Also, it has been discovered that the 1:b ratio in the product increases with increasing ligand:rhodium ratio. For example, phosphine-type ligands, including specifically and for example triphenylphosphine, are customarily employed in rhodium-catalyzed hydroformylation systems in proportions such that the ratio of phosphorus to rhodium is at least about 10:1, ranging on upwardly to as much as 1000:1. Ratios lower than about 2:1 have been found to be less satisfactory. As the phosphorus:rhodium ratio is increased in the systems employing the previously-recognized ligands such as triphenylphosphine, there is a gradual improvement in the 1:b ratio in the product aldehydes indicative of an equilibrium-type reaction. Thus, it is customary to use a substantial excess of ligand. However, it has been found that as the triphenylphosphine ligand concentration is increased, the rate of hydroibrmylation decreases and losses of the ligand increase due to volatilization. The latter problem becomes worse as the size of the alkene being hydroformylated increases.

It has long been desired to tailor a catalyst system that would simultaneously provide high rates of reaction thereby reducing rhodium requirements, be selective for the linear aldehyde and be stable so as to maintain the activity of rhodium. To a certain extent, there has been substantial progress in tailoring such a rhodium catalyst system whereby a bidentate ligand is used for binding with the rhodium. The effective use of such ligands in stoichiometric ratios has obviated the need for high ligand concentrations and reduced the resultant ligand losses such as due to volatilization, precipitation and the like. Accordingly, numerous bidentate ligands have been studied whereby an organic moiety L is substituted with at least two phosphino groups, usually phosphinomethyl groups. The bidentate ligands which have been studied include those wherein the organic moiety, L, is cycloalkylene, i.e., ferrocene, cyclobutane, cyclopropane and norbornane as well as phenylnaphthalene, biphenylene and binaphthalene, wherein the moiety L is usually substituted with two phosphino groups, typically, diphenylphosphinomethyl groups. Among U.S. patents which describe such bidentate ligands are U.S. Pat. No. 4,139,565 to Unruh et. al. which discloses a bidentate ligand containing an organic moiety L including cyclopropane, cyclobutane, cyclopentane, phenanthrene and decalin; U.S. Pat. No. 4,152,344 to Unruh directed to diphosphinoferrocene and U.S. Pat. No. 4,755,624 to Phillips et. al. which is directed to diphosphino binaphthalene ligands. Further as disclosed in Casey et. al., "Diphosphines with Natural Bite Angles near 120° Increase Selectivity for n-Aldehyde Formation in Rhodium-Catalyzed Hydroformylation," *Journal of the American Chemical Society* 1992, 114, 5535–5543 other diphosphino ligands including those in which the organic moiety L is biphenyl, cyclopropane, norbornane, etc. have been suggested.

It has been found that certain of these bidentate phosphino ligands indeed provide high selectivities to the n-aldehydes at stoichiometric concentrations of the ligand, for example, 1,1'-bis(diphenylphosphino)ferrocene and trans- 1,2 bis-(diphenylphosphinomethyl)cyclobutane (t-DPCB). These useful ligands were then modified by placing electron withdrawing groups on the phenyl groups attached to the phosphorus atoms in an attempt to increase the linear to branched (1:b) aldehyde ratio. U.S. Pat. Nos. 4,221,7444 and 4,152,344 to Unruh are examples of patents showing the addition of electronegative substituents to the bidentate ligands. It has been shown that the electron withdrawing groups increase the 1:b-aldehyde ratio. A particular example of a useful bidentate ligand was ferrocene containing p-$CF_3$ on the phenyl groups attached to the phosphorus. Linear to branched aldehyde ratios of 22:1 with reaction rates 10 times faster than the triphenylphosphine system were achieved.

Unfortunately, the catalyst also deactivated at an unacceptable rate. It was further shown, however, that although a cyclobutane ligand did not appear to deactivate, it was not readily known how to put electronegative substituents on the phenyl groups in the cyclobutane system in a practical manner as the synthetic approach had to be different than for the ferrocene ligand system. While British Patent No. 1,452,196 presents a useful discussion of the synthesis of ligands having two phosphinomethyl moieties attached to cyclic structures, the patent does not disclose such synthesis wherein an electronegative-substituted moiety is incorporated into the diphosphinomethyl ligands.

Accordingly, bidentate ligands, and particularly diphosphino ligands, have come to be recognized as an advance over the relatively simple ligands, normally monodentate, which until recently have been considered typical and entirely satisfactory.

The industry continues, however, to seek further improvement in these rhodium-complex hydroformylation catalyst systems for several reasons which include (a) the recognition that any measures for reducing reaction pressure and temperature without suffering a loss in reaction conversion rate and 1:b ratio in the product will greatly reduce operating cost and (b) rhodium and the ligands both being costly, anything to improve catalyst efficacy and catalyst longevity will reduce both operating costs and investment cost.

It is also to be kept in mind, of course, that the supply of rhodium available throughout the world is limited, so that obtaining maximum productivity per unit amount of rhodium-based catalyst is in itself a matter of unusual importance.

It is an object of this invention to provide new bidentate ligands for use in rhodium-catalyzed hydroformylation processes, the use of which facilitates operation at lower catalyst concentrations than are required with prior-art ligands.

It is another object of the present invention to provide an improved hydroformylation process employing catalysts comprising rhodium hydridocarbonyl in complex combination with novel bidentate organic ligands, in particular diphosphino ligands.

It is a further object to provide a method of general applicability for improving the efficacy of a given ligand by incorporating into its molecule certain substituent moieties which have now been found to have the effect of improving its efficacy in hydroformylation reaction systems.

Still another object of the invention is to provide methods of synthesis for producing certain cyclic bidentate ligands containing electronegative substituents.

Other objects will be apparent from the following specification.

SUMMARY OF THE INVENTION

In accordance with the present invention, novel bidentate phosphine ligands are provided which are particularly useful in hydroformylation. The novel ligands of this invention can be represented by the formula:

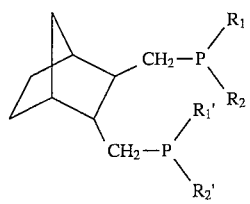

$R_1$, $R_2$, $R_1'$ and $R_2'$ are organic radicals at least one of which contains an electronegative substituent moiety and the methylene groups are present in the trans 2,3 positions. The novel ligands of this invention are useful in hydroformylating an ethylenically-unsaturated compound, e.g., an alkene, to form an aldehyde derivative thereof by reaction with a carbon monoxide-hydrogen synthesis gas in the presence of a liquid reaction medium which contains, as the hydroformylation catalyst, rhodium hydridocarbonyl in complex combination with the novel bidentate ligand of this invention. It is preferred that there be maintained in the liquid reaction medium contained in the hydroformylation reaction solvent at least about 1.5 moles of the ligand per atom of rhodium. That is, the ratio of phosphorus atoms to rhodium atoms in the catalytic complex should be at least about 3.0:1.0.

It will be understood that carbon monoxide and hydrogen are themselves ligands in the present catalyst systems, but the term "ligand" or "additional organic ligand" will be used hereinbelow to designate the novel bidentate ligands of this invention which can be employed in addition to carbon monoxide and hydrogen to make up an improved hydroformylation catalyst system.

The novel ligands of the invention as represented above contain norbornane with trans methylene groups in the 2,3 position in combination with electronegative moiety-substituted "R" groups attached to the phosphorus atoms. The improved ligands of the present invention have been found to increase the rate of hydroformylation of alkenes relative to the commercial standard ligand comprising triphenylphosphine. Moreover, running the hydroformylation reaction using the novel ligands yields a product which contains normal and branched-chain aldehyde derivatives of the olefinic feedstock in which the 1:b ratio is satisfactory and selectivity to the 2-olefin is reduced under otherwise-identical reaction conditions of pressure, catalyst concentration, etc., at ligand concentrations substantially less than those used when the prior art triphenylphosphine ligand is used.

It will be recognized that employment of the present improved catalyst complexes does not require a knowledge of the exact manner in which the rhodium is incorporated into the complete catalytically active complex. Broadly, it is known that the rhodium is in complex combination with ligands comprising carbon monoxide and an additional organic ligand. More specifically, the catalytically-active complex is considered to be rhodium hydridocarbonyl in complex combination with an additional ligand (i.e., the improved ligands which are central to the present invention), but the present invention does not reside in any particular theory as to how the rhodium complex is structured.

Aside from the employment of the present novel ligand, the hydroformylation reaction conditions which can be used in processes employing the novel ligand are those of the prior art as already generally understood, although it is not necessary to employ catalyst concentrations as high as normally used in the prior art.

The present invention also provides novel phosphino compounds which are useful intermediates in forming the bidentate ligands of this invention and, as well, provides a novel synthesis route for adding electronegative-substituted phosphines to cyclic compounds such as norbornane.

DETAILED DESCRIPTION OF THE INVENTION

The novel ligands of the present invention include, broadly, ligands which have at least two phosphino groups and are represented by the formula:

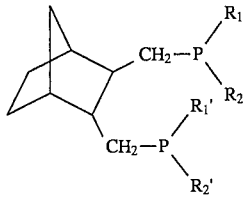

wherein $R_1$, $R_2$, $R_1'$ and $R_2'$ are organic, normally hydrocarbyl groups and wherein the methylene groups are present at the trans 2,3 positions. Arsenic or antimony analogs of the phosphino-based ligands can also be employed, although the phosphino ligands are of particular industrial importance, so the present improvements are directed primarily to them.

$R_1$, $R_2$, $R_1'$ and $R_2'$ can be alike or different, although as a practical matter they will ordinarily be alike since the synthesis of ligands in which these groups are different from one another is comparatively difficult and the use of mixed phosphino substituents is not believed to provide an additional advantage. Normally, $R_1$, $R_2$, $R_1'$ and $R_2'$ are hydrocarbyl groups, preferably of from 1 to about 20, and especially from 1 to about 12 carbon atoms. They may be alkyl, aryl, cycloalkyl, aralkyl or alkaryl, but phenyl groups are specifically useful and the precursor compounds required for synthesizing the bis(diphenylphosphino) ligands are readily available. Alternatively, $R_1$, $R_2$, $R_1'$ and $R_2'$ can be simple alkyl groups, especially of from about 1 to about 12 carbon atoms, since precursor compounds for synthesizing phosphino moieties containing such lower alkyl groups are also available.

The electron withdrawing moieties which are to be attached to the hydrocarbyl groups attached to the phosphorus atoms in the ligands are preferably characterized by having a positive Hammett's sigma value as explained in Gilliom, R. D., *Introduction to Physical Organic Chemistry*, Addison-Wesley, 1970, Chapter 9, pp. 144–171. Preferably, the electronegative moiety should be attached to the hydrocarbyl group at a position such that the substituent moiety will be separated from the phosphino phosphorus atom by not more than about six carbon atoms. When the hydrocarbyl radical is aryl, as exemplified by the phenyl radical which is particularly suitable for the present purposes, the substituent moiety is preferably in the meta or the para position except, however, that, when the substituent moiety is an alkoxy or hydroxyl group, then the substituent is preferably attached at the meta position. This is consistent with the preferred embodiment set forth above that the Hammett sigma value be positive. Alkoxy and hydroxyl moieties in the para position have a negative Hammett sigma value, and acetylamino and phenyl groups are also negative in the para position. While these substituents can be used, such moieties are not preferably positioned.

While it is to be understood that, as already explained, any substituent moiety having a positive Hammett sigma value can preferably be used, the following substituent moieties are especially preferred and illustrative: m-fluoro; di-m-fluoro; p-fluoro; p-trifluoromethyl; m-trifluoromethyl; di-m-trifluoromethyl; p-chloro; m-chloro; p-bromo; m-bromo; p-nitro (but only with exercise of caution in preparing and storing); p-cyano; and m-methoxy, ethoxycarbonyl, acetoxy, acetyl, acetythio, methylsulfonyl; methylsulfanyl; sulfamoyl, and carboxy.

The benefits of inserting the above-described substituent moieties into the hydrocarbyl (or, more broadly, organic) groups which are attached to the phosphino phosphorus atoms are to some extent achieved when even one of the four R groups is so substituted. The beneficial effect is additive, however, (although not necessarily linear), so that it is preferred that all four R groups have the electronegative substituents. Commonly, $R_1$, $R_2$, $R_1'$ and $R_2'$ will be identical and each of these groups will also have the same electronegative substituents attached to it. This is not essential, however, as the use of mixed R groups also having mixed electronegative substituents is not intended to be excluded.

While alternatives and/or modifications may suggest themselves to those skilled in the art, the preparation of the electronegatively-substituted diphosphino norbornane ligands for use in the present improved process may be outlined as follows:

One begins with the Grignard reagent corresponding to the electronegatively-substituted moiety desired to be incorporated into the diphosphino ligand which is ultimately to be synthesized. That is, for example, when it is desired that the electronegatively-substituted "R" in the final ligand product is to be p-trifluoromethylphenyl, one begins with the Grignard reagent which is made from p-trifluoromethylbromo benzene. The Grignard reagent is then reacted with a dialkylphosphite $(R^3O)_2P(O)H$ to form a phosphine oxide wherein $R^3$ is an alkyl group of from 1 to 5 carbon atoms. The reaction, for example, with the diethyl phosphite can be that as set forth in (I) below:

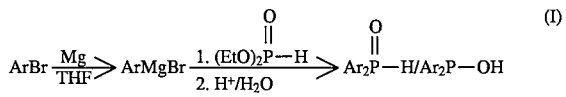

wherein Ar is an electronegatively-substituted phenyl, THF is tetrahydrofuran, and Et is ethyl.

Certain of the electronegatively-substituted intermediates which can be formed by the above process are new compounds, i.e., bis(3,5-difluorophenyl)phosphine oxide. Bis(3,5-difluorophenyl)phosphine oxide is one of only a very few secondary phosphine oxides that can be isolated as the phosphinous acid and be interconverted between the secondary phosphine oxide and the phosphinous acid. The phosphine oxide is then reduced with a reducing agent such as $LiAlH_4$, phenylsilane, diphenylsilane, etc. to form the phosphine. Bis(3,5-difluorophenyl)phosphine is a novel compound and a useful intermediate for forming the norbornane ligand of this invention.

The 2,3-dimethylene norbornane moiety is readily prepared by known and published methods and as such the process of forming same does not particularly form a part of the present invention. In brief, the process involves reacting cyclopentadiene with diethyl fumarate and hydrogenating the product to form a bis-substituted norbornane derivative. To form the bis-phosphine ligand of the present invention, it has been found useful that the dimethylene norbornane moiety be in the form of a disulfonic acid ester thereof. The preferred disulfonic acid esters are the di-mesylate and di-tosylate formed by reacting the trans-2,3-bis-(hydroxymethyl)norbornane with the respective sulfonic acid chloride. Preparation of the di-mesylate derivative of dimethylene norbornane moiety is shown in reaction scheme (II)

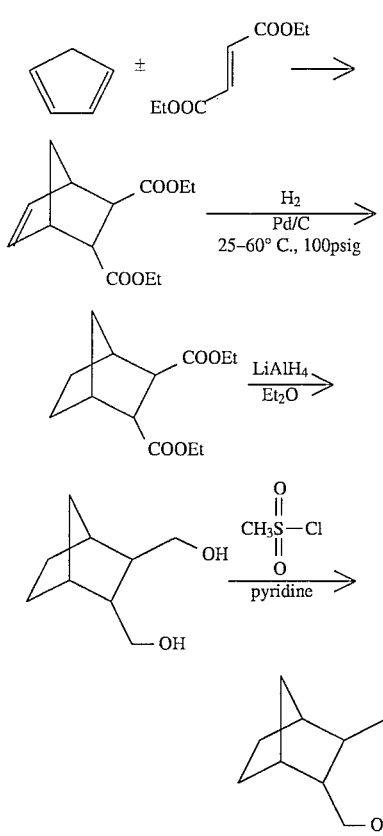

wherein Ms is mesyl.

The bis-phosphine ligands of the present invention are formed by reacting the disulfonic acid ester of the dimethylene norbornane moiety such as formed by the reaction scheme (II) with an alkali metal phosphide of formula $R_1R_2PM$ alone or with a second phosphide of formula $R_1'R_2'PM$ wherein M represents an alkali metal. The alkali metal phosphide is formed in-situ from reaction of the secondary phosphine (itself having been formed by reduction of the phosphine oxide of reaction (I)) and an alkali metal or the hydride thereof, e.g., KH in an inert solvent such as tetrahydrofuran. It is important, if not critical, to achieve efficient coupling of the phosphine moiety to the di-methylene norbornane backbone to run the coupling reaction at below −20° C., preforably at about −75° C. (dry ice/acetone bath) and to add rapidly and sequentially the KH and the di-sulfonic acid ester of dimethylene norbornane to the phosphine solution. It may be possible to have both the di-sulfonic acid ester of the dimethylene norbornane moiety and the phosphine in solution prior to the addition of the KH, since KH apparently does not react with the sulfonic acid ester. It is important, however, to have a reactant in solution other than the alkali metal phosphide since the alkali metal phosphide will react with itself. For example, potassium bis(3,5-difluorophenyl)phosphide produces a mixture of isomers consisting of about 90% 1,2-bis[bis(3,5-difluorophenyl)phosphino]-5-fluorobenzene and about 10% 1,3-bis [bis(3,5-difluorophenyl)phosphino]-5-fluorobenzene.

The length of time the reaction is kept at the low temperature is also important, particularly for the highly electron-withdrawing moieties such as 3,5-difluorophenyl. For such ligands, the reaction mixture should be kept cold for at least about 8 hours. Typically, the reaction should be kept cold for at least about 10–12 hours. One reaction for coupling the phosphine to the dimethylene norbornane is set forth in reaction (III).

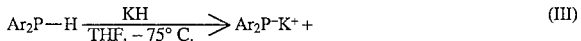

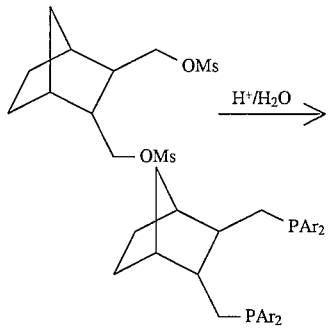

Incorporating the ligand into the complete catalytic complex comprising the ligand and rhodium hydridocarbonyl can be carried out by methods already known to the art as exemplified, for example, by the disclosure of Belgian Pat. No. 840906, issued Oct. 20, 1976. Advantageously, for example, a rhodium compound containing a carbonyl moiety in the molecule, as exemplified by rhodium carbonyl $Rh_4(CO)_{12}$ or similar variant, is simply mixed with the ligand in a suitable inert liquid, which conveniently can be the solvent which is to be used in the subsequent hydroformylation reaction itself (e.g., toluene or a liquid alkane or any of the many known hydroformylation reaction solvents including liquids comprising predominantly the hydrocarbon reactants and/or the hydroformylation reaction products themselves, which are usable as hydroformylation liquid reaction media even though they are not, strictly speaking, chemically inert). The resulting mixture of ligand and rhodium carbonyl can then simply be injected directly into the hydroformylation reaction zone, where, in the presence of hydrogen/carbon monoxide synthesis gas and under the conditions of pressure and temperature normally obtained in hydroformylation reaction systems, the formation of the desired catalyst complex is completed.

Another useful rhodium source in forming the catalytic complex is hydrocarbonyltris(triphenylphosphine)rhodium(I), or $HRh(CO)(PPh_3)_3$. This is itself, of course, a complex of rhodium hydridocarbonyl with a ligand (triphenylphosphine). To be industrially attractive in hydroformylation reactions, however, it must be used with a substantial excess of the triphenylphosphine (i.e., substantially more than a 3:1 ratio of triphenylphosphine to rhodium). By using $HRh(CO)(PPh_3)_3$ as the rhodium source, however, in an improved complex wherein the present improved ligand is also a component, one obtains a greatly improved catalyst in which the triphenylphosphine moiety is only a diluent and contributes little if anything to the efficacy of the mixture. Other rhodium sources which can be used include: rhodium on carbon, $Rh_2O_3$, $Rh(NO_3)_3$, $Rh_2(SO_4)_3$, $Rh_4(CO)_{12}$, $Rh(CO)_2$ acetoacetonate, $RhCl_3$·$3H_2O$, $RhClCO(PPh_3)_2$, $[Rh(CO)_2Cl]_2$, $[Rh(2,5-cyclooctadine)Cl]_2$, $RhBr_3$, and $RhI_3$. If a halogen-containing rhodium source is to be employed, it is desirable to include with it a sufficient quantity of an alkaline reactant (e.g., sodium hydroxide) to scavenge the halide moiety out of the system as the complex is formed. Other sources of rhodium will also suggest themselves to one skilled in the art and are discussed further hereinbelow.

As just explained, the complex is formed by introducing the ligand and the rhodium source into the hydroformylation reaction zone wherein, under the conditions obtained therein, the catalytically active complex is formed in the presence of the synthesis gas. Enough ligand should be employed that the resulting mixture of ligand and rhodium contains at least about 3.0 phosphino moieties per atom of rhodium. A lower phosphorus:rhodium ratio results in reduced catalytic effectiveness, but these ligands are quite effective at phosphorus:rhodium ratios as low as 3.0:1. That is, there is a very definite increase in catalytic effectiveness of the ligands as the phosphorus:rhodium ratio is increased up to 3.0:1; the effect of further increases in the ratio is less pronounced. It is, of course, always desirable to maintain a phosphorus:rhodium ratio at least slightly above 3:1 in order to be sure that the ratio does not inadvertently fall below this desired level as a result of, for example, metering errors that might occur in the course of adding rhodium and ligand to a reactor, especially at low flow rates.

As is already well understood in the existing art, the hydroformylation of an olefinic feedstock, e.g., an alkene, by a process of the present type is effected by introducing into a reaction zone contained in a reaction vessel of conventional type the olefin to be hydroformylated (in either gas or liquid form) along with a gaseous mixture of hydrogen and carbon monoxide. The reaction vessel contains a liquid reaction medium in accordance with the well-known technology of hydroformylation chemistry as further discussed hereinbelow, and the catalytic complex is dissolved or suspended in this liquid reaction medium. Toluene exemplifies the usual inert solvents or reaction media used in these systems, but many other liquids can be employed, such as benzene, xylene, diphenyl ether, alkanes, ethers, ether oligomers (i.e., UCON oils), poly($\alpha$-olefin) oligomers, aldehydes and esters, the aldehydes and esters often conveniently comprising products and/or byproducts of the hydroformylation reaction itself. Selection of the solvent is outside the scope of the present invention, which is drawn more particularly to improving the catalysts for these reaction systems rather than other modifications of the system itself. In the reaction zone the catalytic complex serves to catalyze the hydroformylation of the olefin with the hydrogen and the carbon monoxide to form a mixture of aldehydes containing one more carbon atom than the olefin reactant. Typically, it is desired to employ a terminally-unsaturated olefin, and it is normally preferred that the terminal carbon atom be the site of attachment of the carbonyl group which is introduced by the hydroformylation reaction. The nature of the catalyst employed affects this matter of whether a normal aldehyde is produced (i.e., whether the terminal carbon atom of the olefin is the site of hydrocarbonylation as compared with the second carbon atom in the chain), and the present improved ligands impart very desirable properties to the hydroformylation catalyst in this regard. That is, they produce a high proportion of aldehyde product in which the terminal carbon atom has been carbonylated.

The olefinically-unsaturated feedstock which is to be hydroformylated by the present improved process can be any of the many types of olefin already known in the art to be suitable for rhodium-catalyzed hydroformylations, especially olefinic compounds having in the molecule up to about 25 carbon atoms. Although monounsaturated compounds are normally employed and are of particular practical importance, di- and tri-ethylenically unsaturated olefins can also be used, the product in each case being, if complete hydroformylation is carried out, a derivative having up to one additional carbon atom for each ethylene double bond in the parent compound. Olefinic compounds having substituted groups, e.g., ethylenically-unsaturated alcohols, aldehydes, ketones, esters, carboxylic acids. acetals, ketals, nitriles, amines, etc., can be easily hydroformylated as well as the simple mono-alkenes which are particularly useful and of particular commercial importance. Broadly, ethylenically-unsaturated compounds which are free of atoms other than carbon, hydrogen, oxygen, and nitrogen are readily hydroformylated, and more particularly compounds consisting solely of oxygen, hydrogen and carbon. Some specific classes of substituted olefins to which the hydroformylation process is applicable are: unsaturated aldehydes such as acrolein and crotonaldehyde; alkanoic acids such as acrylic acid; and unsaturated acetals, such as acrolein acetal. Formaldehyde can also be hydroformylated by the present process. More commonly, suitable hydroformylation feedstocks include the simple alkenes such as ethylene, propylene, the butylenes, etc.; alkadienes such as butadiene and 1,5-hexadiene; and the aryl, alkaryl, and aralkyl derivatives of the foregoing. Lower mono-alkenes of 2 to about 12 carbon atoms are especially useful. Hydroformylation does not normally take place within the benzene ring of olefins having aryl substitution, of course, but rather in the ethylenically unsaturated portion of the molecule.

Process operating parameters to be employed in practicing the present process will vary depending upon the nature of the end product desired, since as already known in the art, variation of operating conditions can result in some variation in the ratio of aldehydes to alcohols produced in the process (some alcohol may be formed in small amounts along with the aldehyde which is normally the desired product) as well as the ratio of the normal to the branched-chain aldehyde derivative of the parent feedstock. The operating parameters contemplated by the present process are broadly the same as those conventionally employed in hydroformylation processes using rhodium complexes as already known in the art. For the sake of convenience, these parameters will be generally set forth hereinbelow with the understanding, however, that the process parameters are not critical to achieve the improved results of the present invention as compared with processes using the prior art ligands and do not, per se, form a part of the invention. That is, the present improvement lies in the use of the present improved ligands and not in the concomitant employment of any change from existing rhodium hydroformylation technology as already known to the art. To repeat the point, using the present improved catalyst system does not necessitate any departure from rhodium-catalyzed hydroformylations as already known, except for changing the ligand.

In general, the hydroformylation process is conducted under a total reaction pressure of hydrogen and carbon monoxide combined of one atmosphere or even less, up to a combined pressure of about 700 atmospheres absolute. Higher pressures can be employed but are normally not required. For economic reasons, however, pressures significantly greater than about 400 atmospheres absolute will not normally be employed.

The reaction is normally conducted at a temperature of from about 50° C. to about 200° C., with a temperature within the range of about 75° C. to about 150° C. being most commonly employed.

The ratio of partial pressures of hydrogen to carbon monoxide in the reaction vessel may be from about 10:1 to about 1:10 in accordance with the prior art, although it has been discovered that when using the present ligands this range may even be extended to about 50:1 to 1:50. Normally, however, the range of hydrogen partial pressure to that of carbon monoxide will be from about 6:1 to about 1:1, with a hydrogen:carbon monoxide ratio of about 2:1 to 1:1 usually being employed.

Whatever may be the composition of the liquid reaction medium (i.e., whether it comprises predominantly a separate reaction solvent or a reaction feedstock or reaction product or by-product), the catalyst complex should be maintained in it at a concentration of about 0.1 to 50 millimoles/L calculated as rhodium. More preferably, about 0.5 to 20.0 millimoles/L of rhodium is recommended. While the catalyst can be formed ex-situ, it is conveniently prepared in-situ in the liquid reaction medium by introducing the ligand along with a suitable rhodium source and then allowing complexation to occur under the temperature to be employed in the hydroformylation reaction and in the presence of the hydrogen-carbon monoxide gas mixture which is to be used in the hydroformylation process.

The following examples are given to illustrate the practice of the invention. It will be understood that many variations can be made therefrom in accordance with the explanations given hereinabove.

EXAMPLE 1

Synthesis of the Diethyl Ester of trans-2,3-Norbornane Dicarboxyic Acid

Following reaction scheme (II), cyclopentadiene was generated from cyclopentadiene dimer in the following way. Dicyclopentadiene (75 g) was charged to a 500 mL round-bottom flask equipped with a magnetic stirring bar and a distilling head. The flask was immersed in an oil bath which was heated to 175° C. The cyclopentadiene distilled over as it was cracked as evidenced by an overhead temperature of 54°–60° C. The receiving flask containing the distilled cyclopentadiene was chilled to 0° C. with an ice bath. In this way 54.9 g (0.83 moles) of cyclopentadiene was made.

The 500 mL 3-necked receiving flask was fitted with a stirring bar, dropping funnel, and a condenser and was immersed in an ice bath. Diethyl fumarate (143.0 g=0.83 moles) was added to the chilled cyclopentadiene via the dropping funnel over a period of about 15 minutes. The ice bath was left on for an additional 30 minutes. It was then removed and the reaction solution was refluxed for an hour, and then allowed to stir overnight at room temperature. The crude reaction mixture was then distilled, collecting the fraction boiling at 102°–112° C. at 2 mm Hg. NMR ($^{13}$C. and $^1$H) confirmed that the product was the desired diethyl norbornene dicarboxylate. The yield was 118.9 g (0.50 moles=60% of theoretical).

The diethyl norbornene dicarboxylate from above was combined with 33 g of another preparation to yield 151.5 g of the diethyl norbornene dicarboxylate. This was hydrogenated to the desired diethyl ester of trans-2,3-norbornane dicarboxylic acid in two batches as follows. A 50 g portion of the diethyl norbornene dicarboxylate was combined with about 50 mL of ethanol and 2.5 g of 5% Pd/C. in a 300 mL stirred autoclave. The autoclave was sealed and pressured to 100 psig with hydrogen. Stirring was started and gas uptake immediately commenced. The temperature rose to 50° C. in about ten minutes, after which gas uptake ceased and the temperature declined. The reaction mixture was stirred for an additional two hours. The autoclave was then opened and the contents were removed. The remainder of the diethyl norbornene dicarboxylate (101.5 g) was hydrogenated in the same manner using 100 mL of ethanol and 4 g of 5% Pd/C. After filtration and removal of ethanol, the crude, saturated dicarboxylate weighed 159 g. It was distilled, collecting the fraction boiling at 108°–115° C. at 2 mm Hg. The yield of pure (by NMR) diethyl ester of trans-2,3-norbornane dicarboxylic acid was 142.5 g (93.2% of theoretical).

EXAMPLE 2

Synthesis of trans-2,3-Norbornanedimethanol

Further following reaction scheme (II), to an oven-dried 1 L 3-necked flask equipped with a magnetic stirring bar, dropping funnel and condenser with a nitrogen inlet tube was added lithium aluminum hydride (13.0 g=0.342 mole) and approximately 300 mL of anhydrous diethyl ether. The diethyl ester of trans-2,3-norbornane dicarboxylate acid (62.5 g=0.260 mole) was dissolved in about 150 mL of anhydrous ether and was added to the 3-necked flask, via the dropping funnel at a rate which maintained rapid reflux. The reaction was carried out under nitrogen. After addition was complete the reaction mixture was refluxed for an additional hour. Then ethyl acetate (20 g=0.22 mole) was added to react with any excess LiAlH$_4$. Next 150 g of 10% aqueous NH$_4$Cl was added slowly. The salts thus produced formed granules which were filtered from the ether solution. The ether solution was dried over MgSO$_4$, filtered, and the ether removed on a roto-evaporator to yield 42.6 g of crude norbornanedimethanol. This was distilled, collecting a very viscous clear liquid fraction boiling at 111°–112° C. at 0.25 mm Hg. The yield of trans-2,3-norbornanedimethanol was 36.2 (89% of theoretical).

EXAMPLE 3

Synthesis of Dimesylate of trans-2,3-Norbomanedimethanol

Continuing the process as shown in reaction scheme (II), trans-2,3-norbomanedimethanol (18.0 g=0.115 mole) was dissolved in 100 mL of anhydrous pyridine under nitrogen in an oven-dried 250 mL 3-necked flask. The flask was placed in an ice bath and methanesulfonyl chloride (27.3 g=0.238 mole) was added dropwise, with stirring, over a period of 30 minutes. The reaction mixture was stirred at 0° C. for an additional 3 ½ hours, poured into excess water and then was acidified to a pH of about 1 with HCl. An oil (which solidified) and crystals fell out of solution. These were filtered off and the mother liquor was washed with methylene chloride (3×75 mL). The solid from above was dissolved in the methylene chloride washings and was extracted with 3N HCl (3× 60 mL), followed by a 5% aqueous solution of NaHCO$_3$ (2×50 mL). Finally it was washed twice with water (the pH of the water washings were neutral). The methylene chloride solution was dried over MgSO$_4$, filtered, and the methylene chloride was evaporated off to yield 35.1 g of the crude dimesylate. The crude dimesylate was crystallized from methanol. Two crops of crystals were obtained which were combined to yield 31.5 g of desired dimesylate (87.8% of theoretical).

EXAMPLE 4

Synthesis of Bis(3.5-Difluorophenyl)phosphinous Acid (Secondary Phosphine Oxide)

In accordance with reaction (I) above, to an oven-dried 250 mL, 3-necked round bottom flask equipped with a magnetic stirring bar, dropping funnel, and a condenser with a nitrogen inlet tube was added magnesium turnings (5.38 g=0.221 mole), 50 mL of anhydrous tetrahydrofuran (THF), and a few crystals of iodine to initiate the Grignard reaction. To the rapidly stirred Mg/THF mixture was added 1-bromo-3,5-difluorobenzene (40.01 g=0.207 mole) in 50 mL of anhydrous THF dropwise from the dropping funnel at such a rate that reflux was maintained (addition took about 70 minutes). The reaction was stirred for an additional 2 hours during which time the reaction mixture darkened and most of the Mg disappeared.

In the meantime, diethylphosphite (7.17 g=0.0520 mole) in about 50 mL of anhydrous THF was placed in an oven dried 250 mL, 3-necked flask equipped with a magnetic stirring bar, condenser with a nitrogen inlet tube and a rubber septum. With rapid stirring the Grignard Reagent from above was transferred dropwise via a canula to the phosphite-containing flask. The solution warmed as the reaction took place. After addition, the reaction mixture was allowed to stir overnight. It takes three moles of Grignard Reagent per mole of phosphite since the first molar equivalent forms the salt, $(EtO)_2POMgBr$. Ratios of 4:1 can be used in case the Grignard reaction was incomplete. It is also possible to determine the amount of diethylphosphite to use based on the concentration of the Grignard Reagent determined by titration. The yield of the Grignard Reagent reaction generally is in the range of 80–95% of theoretical.

After stirring overnight, about ⅔ of the THF was removed and was replaced with ether. Then 100 mL of 10% $H_2SO_4$ was added dropwise. Considerable foaming and a solid formed at first. After all of the acid had been added, no solid was left. The layers were separated, the aqueous layer was washed twice with ether, and the combined organic layers were dried over $MgSO_4$. The ether was then evaporated on a roto-evaporator to yield 17.06 g of a yellow solid. Treatment with 100 mL of boiling ether, followed by filtration left 8.8 g of white solid. Concentration of the ether to about 50 mL resulted in precipitation of 2.6 g more of white solid which was combined with the 8.8 g. The yield of the desired bis(3,5-difluorophenyl)phosphinous acid was 10.4 g (73% based on diethylphosphite).

Identification of the phosphinous acid was made as follows. The phosphinous acid from above had a melting point of 149° C. and the proton decoupled $^{31}P$ NMR spectrum consisted of two peaks, one at +16.95 ppm and the other at +31.34 ppm relative to external phosphoric acid. When the spectrum was run proton coupled, only the peak at +16.95 split, indicating that it was the bis(3,5-difluorophenyl)phosphine oxide. The other peak was the actual bis(3,5-difluorophenyl)phosphinous acid. A small portion of the white solid was distilled in the Kugelrohr at 180° C. and 0.3 mm Hg. The distillate solidified and now had a melting pt. of 64° C. $^{31}P$ NMR showed it to be only the secondary, phosphine oxide. This means that the phosphinous acid form is stable in this case, and that it is convertible to the secondary phosphine oxide. This is believed to be only the second such known compound (bis(trifluoromethyl)phosphinous acid being the other). Also, this secondary phosphine oxide is quite soluble in ether, but when kept cold will gradually precipitate in the phosphinous acid form.

The one part of the procedure which is not general is that of purification of the phosphinous acids. Ordinarily these compounds are not stable and would not be distilled. Generally they were reduced to the secondary phosphine prior to distillation.

EXAMPLE 5

Synthesis of Bis(3.5-difluorophenyl)phosphine

Bis(3,5-difluorophenyl)phosphinous acid (4.78 g=0.0174 mole) was placed in a 50 mL round bottom flask equipped with a magnetic stirring bar and a condenser with a nitrogen inlet tube. To this was added phenylsilane (1.54 g=0.014 mole). With stirring, the reaction was heated to 130° C. for three hours. As the temperature rose, the mixture became homogeneous and remained as such. After three hours, the reaction mixture was distilled, collecting the fraction boiling at 128°–138° C. at 0.05 mm Hg. The yield of bis(3,5-difluorophenyl)phosphine was 2.45 g (54%). The $^3P$ absorption is at −37 ppm (relative to external $H_3PO_4$).

EXAMPLE 6

Synthesis of trans-2,3-Bis[bis(3.5-difluorophenyl) phosphinomethvl]norbornane

Bis(3,5-difluorophenyl)phosphine (2.45 g=0.0095 mole) was dissolved in 50 mL of anhydrous THF in an oven-dried Schlenk flask under nitrogen. The flask was equipped with a stirring bar. The solution was chilled to −70° C. with dry ice/acetone and to it was added rapidly and sequentially potassium hydride (0.4 g=0.010 mole) and the norbornane dimesylate (1.37 g=0.00439 mole) of Example 3. The mixture was stirred rapidly at ±70° C. for about 10 hours, was then allowed to warm up to room temperature and was stirred at room temperature overnight. The solution was golden yellow with a gelatinous precipitate. About ⅔ of the THF was evaporated off under a stream of nitrogen. Ether and 10 mL of 6.5% aqueous $H_2SO_4$ was added and the gel dissolved. The layers were separated, the aqueous layer was washed with ether, and the combined organic layers were dried over $MgSO_4$. After filtration of the $MgSO_4$, the solvent was evaporated off to yield 2.94 g of a white oil which slowly crystallized. $^{31}P$ NMR showed the sample to be the title diphosphine ligand. The absorption for the two phosphorous atoms are at −14.99 and −15.68 ppm (relative to external $H_3PO_4$). The sample also contained a small amount of an all aromatic diphosphine. The yield of 2.94 g was 85% of the theoretical.

If the above reaction sequence is followed except that it is run at room temperature, the isolated phosphine containing product was the all aromatic diphosphines: 1,2-bis[bis(3,5-difluorophenyl)phosphino]-5-fluorobenzene and 1,3-bis[bis(3,5-difluorophenyl)phosphino]-5-fluorobenzene. Synthesis of this mixture is set forth below in Example 7.

EXAMPLE 7

Synthesis of 1,2-Bis[bis(3,5-difluorophenyl)phosphino]-5-fluorobenzene

To an oven-dried 100 mL Schlenk flask equipped with a magnetic stirring bar and under nitrogen was added bis(3,5-difluorophenyl)phosphine (4.35 g=0.0169 mole) dissolved in 50 mL of anhydrous tetrahydrofuran (THF). With rapid stirring, KH (0.70 g=0.0175 mole) was added to the above Schlenk flask. The solution frothed as $H_2$ was released and the reaction mixture turned orange. The reaction mixture was stirred overnight. Then, the THF was reduced to about ⅓ of its volume in a stream of nitrogen, followed by addition of about 30 mL of ether and 20 mL of dilute sulfuric acid. The layers were separated and the aqueous layer was washed with another 20 mL of ether. The combined ether layers were dried over $MgSO_4$, filtered, and the solvent removed on a rotoevaporator. Finally, it was heated on the Kugelrohr at 80° C. and 0.1 mm to yield 3.05 g of a yellowish white solid.

$^{31}P$ NMR showed it to consist of about 90% of the title compound and 10% of the isomer in which the phosphorous atoms are in the 1 and 3 positions. The yield was 89% of theoretical assuming that it takes three moles of bis(3,5-difluorophenyl)-phosphine to produce one mole of the bisphosphine. The $^3P$ signals came at −1.83 and −2.63 ppm (relative to external $H_3PO_4$) for the unsymmetrical ortho-compound and at −4.02 ppm for the symmetrical meta-compound.

Mass spectral analysis also supported the structure. In particular, the molecular weight was found to be 608. Apparently, the first step is disproportionation of the two molecules of the potassium phosphide to produce a dipotassium phosphide and a tertiary phosphine. HF is then eliminated to form a benzyne intermediate which reacts with a molecule of secondary phosphine.

EXAMPLE 8

The norbornane ligands below were formed by the equivalent procedures as set forth in Examples 1–6 above. While the by-products of the other substituted norbornane ligands were not determined, it was found that the reaction mixtures of the respective phosphine and norbornane dimesylate had to be maintained at −70° C. for at least 8 hours or the yield and purities of the ligands were dramatically effected. The acronyms used for the norbornane ligands of this invention and control ligands are as follows:

t-3,5DFNB=trans-2,3-Bis[bis(3,5-difluorophenyl)phosphinomethyl]norbornane t-3FNB=trans-2,3-Bis[bis(3-fluorophenyl)phosphinomethyl]norbornane t-2,5SDFNB=trans-2,3-Bis[bis(2,5-difluorophenyl)phosphinomethyl]norbornane t-CF$_3$NB=trans-2,3-Bis[bis(4-trifluoromethylphenyl)phosphinomethyl]norbornane t-DPNB=trans-2,3-Bis[bis(diphenyl)-phosphinomethyl]norbornane NMR was primarily used to identify the ligands. The $^{31}$P absorptions for the other ligands were as follows (all relative to external $H_3PO_4$ and in $CDCl_3$). $^{13}$C and $^1$H NMR corroborated these results.

t-3,5DFNB: −14.99 and −15.79 ppm t-DPNB: −18.56 and −19.35 ppm t-3FNB: −17.91 and −18.38 ppm t-pCF$_3$NB: −18.21 and −18.85 ppm t-2,5DFNB: multiplets centered at about −38 ppm; could not separate the two phosphorous atoms.

EXAMPLES 9–13

The Examples presented below examine the hydroformylation of 1-hexene to heptanal using various diphosphine ligand systems including the bisphosphine norbornane ligands of the present invention. The hydroformylation studies were done in a batch constant temperature/pressure stirred autoclave. The experimental procedure which was used was as follows:

The stirred autoclave was charged with the Rh source, either $Rh_2(CO)_2AcAc$ or $Rh_4(CO)_2$ ligand, and toluene (the solvent). The autoclave was sealed, flushed with the 1:1 $H_2$:CO blend, pressurized to somewhat below the desired operating pressure, heated and stirred. 1-Hexene was charged to a 1-hexene reservoir. After the autoclave temperature was equilibrated, the 1-hexene was quickly pressured into the autoclave with 1:1 $H_2$:CO blend and the autoclave immediately brought to the desired operating pressure. This point was taken to be time zero. The progress of the reaction was followed by the pressure drop in the high pressure $H_2$:CO reservoir. 1-Hexene conversion was generally taken through 4 to 8 half-lives (94–99.6% conversion). The pressure in the autoclave generally varied by ±1 psig. Temperature variation was ~±1° C. When $H_2$:CO ratios other than 1:1 were desired, the autoclave was first pressured with the gas in excess. The remainder was made up with the 1:1 $H_2$:CO blend. The 1:1 blend was then fed to the reactor on demand, thereby maintaining constant partial pressure of the two gases throughout the run.

After completion of the reaction, the reaction solutions were analyzed by gas liquid chromatography.

In general, the rates of hydroformylation with the norbornane ligands of the present invention were found to be excellent, with rates, depending on the substituents on the phenyl groups, ranging from about 3 to 20 times that of an Rh/TPP control catalyst (50% TPP, 110° C., 125 psi, 1:1 $H_2$:CO). For comparison purposes, the rate constant for the control process is 0.026 min.$^{-1}$. In view of the high reaction rates which were found, selectivities to heptanal (1-aldehyde) of 85–86% were excellent. An exception to the excellent results found were recorded upon use of the 2,5-difluorophenyl ligand which will be discussed below. Similarly, conditions could be found that resulted in low selectivities of the unwanted product, 2-hexene, of less than 2–3%. The 1:b-aldehyde ratios generally ranged from about 6–8:1.

In the Tables below, hexane selectivities are in the range of 1–2%. It was found that the hexane concentration in the 1-hexene feed accounted for most of the hexane found in the product. Actual hexane selectivities under most of the conditions should thus be in the range of 0.1–0.3%.

EXAMPLE 9

Trans-2,3-bis[bis(3-fluorophenyl)phosphiromethyl]norbornane (t–3FNB)

Table I tabulates the hydroformylation results for t–3FNB. It can be seen that the best combination of heptanal selectivity (85.5%) and 1:b-aldehyde ratio (6.8) was in run 6. In this case $k_{obs}$ was 0.122 min$^{-1}$ or about 5 times faster than Rh/50% TPP. The conditions of this run were 100° C., and 150 psi of 1:1 $H_2$:CO. The heptanal selectivity would probably be closer to 86.5% if it were corrected for hexane in the feed.

There were other conditions that lead to higher rates (runs 3 and 7), but the heptanal selectivity was reduced. In fact, in run 7, the rate was 16 times faster than Rh/TPP. With all of the different conditions investigated, the 1:b-aldehyde ratio remained surprisingly constant.

EXAMPLE 10

Trans-2,3-bis[bis(3,5-difluorophenyl)-phosphinomethyl] norbornane (t–3,5-DFNB)

Table II contains the results for hydroformylation with this ligand. The same pattern was obvious here as in the 3-fluoro ligand above. The best combination of heptanal selectivity (85%, corrected for hexane in the hexene feed) and 1:b-aldehyde ratio (7.2) was
Trans-2,3-bis[bis( 4-trifluoromethylphenyl)-phosphinomethyl]norbornane (t-CF$_3$NB )

Table III tabulates the data for t-CF$_3$NB ligand. The optimal run appeared to be run 5 which was carried out at 110° C. and 150 psi of 2:1 $H_2$:CO. The heptanal selectivity was about 84.5% after correction for hexane, and the rate was about 12 times that of the control Rh/TPP run ($k_{obs}$=0.32 min$^{-1}$ vs 0.026 for Rh/TPP). The 1:b-aldehyde ratio was 7:1. Rates 20 times higher than the Rh/TPP control were obtained under certain conditions (run 9), but with loss of heptanal selectivity and 1:b-aldehyde ratio.

EXAMPLE 12

Trans-2,3-bis[bis(2,5-difluorophenyl)-phosphinomethyl]norbornane (t-2.5DFNB)

Table IV contains the data for t-2,5DFNB. $Rh(CO)_2acac$ was used as the Rh source, and as run 1 shows, the results were quite poor. The conversion was only about 50% and most of that was 2-hexene (71%). The l:b-aldehyde ratio was only 3.5:1 with only 22% selectivity to heptanal. In fact, there was so little gas uptake that a rate constant was not determined. It was assumed that the reason for the poor results was that t-2,5DFNB was not a strong enough ligand to displace the acetylacetonate ligand (acac). Therefore, several Rh sources which do not contain acac, i.e., $HRh(CO)(PPh_3)_3$ and $Rh_4(CO)_{12}$ were tried.

$HRh(CO)(PPh_3)_3$ at 110° C. and 150 psi of 1:1 $H_2$:CO resulted in reasonable heptanal selectivities and l:b-aldehyde ratios (runs 2 and 3), but the rate was low with $k_{obs}$ being only about 0.01 min$^{-1}$ or about 40% of the control Rh/TPP rate. The $Rh_4(CO)_{12}$ at 110° C. and 150 psi of 2:1$H_2$:CO resulted in about twice the rate of the hydridorhodium complex, and somewhat better heptanal selectivity and l:b-aldehyde ratio (runs 7 and 11).

Several additives with $Rh(CO)_2(acac)$ were tried to see if the acac ligand could be forced off of the metal. Runs 6 and 8 used 20 microliters and 40 microliters of 48% $HBF_4$, respectively, for this purpose. It can be seen that 20 microliters of $HBF_4$ were reasonably successful at removing acac if run 6 is compared to run 2 (hydridorhodium complex). However, increasing the acid addition to 40 microliters resulted in poorer selectivities and rates.

Hydrazine hydrate was also used as an additive (runs 4 and 5). It can be seen that hydrazine offered little help in removing acac.

EXAMPLE 13

1,2-Bis[bis(3,5-difluorophenyl)phosphino]-5-fluorobenzene

In this example, the compound formed in Example 7 was used to hydroformylate 1-hexene. Table V sets forth conditions and results. l:b ratios of product were excellent, although selectivity to heptanal and reaction rate were slightly sacrificed.

TABLE I

1-Hexene Hydroformylation Results using Norbornane Ligand t-3FNB[1]

| Run | Catalyst[2] (mmoles) | Ligand (mmoles) | Rxr Temp. (°C.) | Rxr Press. (psig) | $H_2$/CO Ratio | Initial 1-Hexene grams | Product wt. % 1-Hexene | Product wt. % Heptanal | Product wt. % 2Mehexal | Product wt. % 2-Hexene | Product wt. % Hexane |
|---|---|---|---|---|---|---|---|---|---|---|---|
| 1 | (0.066) | (0.27) | 110 | 150 | 2:1 | 13.36 | 0.08 | 20.82 | 3.20 | 0.37 | 0.26 |
| 2 | (0.054) | (0.22) | 110 | 150 | 1:1 | 13.89 | 0.59 | 16.34 | 2.57 | 0.24 | 0.19 |
| 3 | (0.054) | (0.22) | 120 | 150 | 1:1 | 13.61 | 0.12 | 17.31 | 2.85 | 0.41 | 0.22 |
| 4 | (0.070) | (0.15) | 110 | 150 | 1:1 | 13.51 | 0.16 | 10.37 | 3.78 | 4.48 | 0.00 |
| 5 | (0.047) | (0.14) | 110 | 150 | 1:1 | 13.84 | 0.23 | 13.35 | 2.90 | 2.16 | 0.22 |
| 6 | (0.056) | (0.23) | 100 | 150 | 1:1 | 13.58 | 0.12 | 18.97 | 2.78 | 0.16 | 0.17 |
| 7 | (0.058) | (0.23) | 117 | 150 | 2:1 | 13.86 | 0.12 | 20.23 | 3.11 | 0.69 | 0.31 |
| 8 | (0.050) | (0.40) | 110 | 150 | 2:1 | 13.48 | 0.29 | 17.42 | 2.65 | 0.35 | 0.27 |
| 9 | (0.058) | (0.24) | 110 | 105 | 2:1 | 13.77 | 0.28 | 17.76 | 2.63 | 0.47 | 0.27 |

| Run | Linear/ Branch Ratio | Percent Select Heptal | Percent Select Br-Prod. | Percent Select 2-Hexene | Percent Select Hexane | Rate Constant (mins.-1/nM Rh) | R value | Percent Hexene Conv. | Percent Mass Acc. |
|---|---|---|---|---|---|---|---|---|---|
| 1 | 6.51 | 83.73 | 12.57 | 2.02 | 1.39 | 0.141 | 0.991 | 99.57 | 111.70 |
| 2 | 6.36 | 83.85 | 13.19 | 1.67 | 1.29 | 0.182 | 0.996 | 96.05 | 84.92 |
| 3 | 6.07 | 82.40 | 13.57 | 2.65 | 1.39 | 0.256 | 0.997 | 99.23 | 92.34 |
| 4 | 2.74 | 51.26 | 18.69 | 30.05 | 0.00 | 0.169 | 0.985 | 98.94 | 86.58 |
| 5 | 4.54 | 68.42 | 15.07 | 15.02 | 1.49 | 0.169 | 0.999 | 98.43 | 84.57 |
| 6 | 6.82 | 85.48 | 12.53 | 0.98 | 1.02 | 0.122 | 0.929 | 99.27 | 92.77 |
| 7 | 6.50 | 81.94 | 12.60 | 3.79 | 1.66 | 0.426 | 0.997 | 99.34 | 106.10 |
| 8 | 6.57 | 83.34 | 12.68 | 2.27 | 1.71 | 0.167 | 0.992 | 98.15 | 96.13 |
| 9 | 6.75 | 83.05 | 12.30 | 2.98 | 1.67 | 0.281 | 0.995 | 98.25 | 92.15 |

[1]t-3FNB = trans - 2,3-Bis[bis(3-fluorophenyl)phosphinomethyl]norbornane
[2]Catalyst = $Rh(CO)_2$ Acetylacetonate

TABLE II

1-Hexene Hydroformylation Results using Norbornane Ligand t-3,5DFNB[1]

| Run | Catalyst[2] (mmoles) | Ligand (mmoles) | Rxr Temp. (°C.) | Rxr Press. (psig) | $H_2$/CO Ratio | Initial 1-Hexene grams | Product wt. % 1-Hexene | Product wt. % Heptanal | Product wt. % 2Mehexal | Product wt. % 2-Hexene | Product wt. % Hexane |
|---|---|---|---|---|---|---|---|---|---|---|---|
| 1 | (0.050) | (0.20) | 110 | 150 | 2:1 | 13.39 | 0.04 | 22.15 | 2.73 | 1.05 | 0.37 |
| 2 | (0.050) | (0.21) | 110 | 105 | 2:1 | 13.84 | 0.10 | 22.24 | 2.57 | 1.57 | 0.43 |
| 3 | (0.050) | (0.21) | 110 | 110 | 1:1 | 13.85 | 0.21 | 24.40 | 3.00 | 1.09 | 0.27 |
| 4 | (0.047) | (0.20) | 100 | 110 | 1:1 | 13.89 | 0.75 | 17.21 | 2.39 | 0.42 | 0.20 |
| 5 | (0.050) | (0.10) | 110 | 110 | 1:1 | 13.79 | 0.49 | 9.41 | 2.86 | 2.00 | 5.16 |
| 6 | (0.054) | (0.22) | 120 | 150 | 1:1 | 13.82 | 0.04 | 14.34 | 1.98 | 0.63 | 0.21 |
| 7 | (0.054) | (0.15) | 110 | 150 | 1:1 | 13.69 | 1.64 | 10.99 | 2.18 | 3.60 | 0.00 |
| 8 | (0.050) | (0.19) | 120 | 150 | 1:1 | 13.59 | 0.05 | 17.49 | 2.40 | 0.79 | 0.26 |

TABLE II-continued

1-Hexene Hydroformylation Results using Norbornane Ligand t-3,5DFNB[1]

| Run | Linear/ Branch Ratio | Percent Select Heptal | Percent Select Br-Prod. | Percent Select 2-Hexene | Percent Select Hexane | Rate Constant (mins.-1/nM Rh) | R value | Percent Hexene Conv. | Percent Mass Acc. |
|---|---|---|---|---|---|---|---|---|---|
| 1 | 8.11 | 82.66 | 10.19 | 5.32 | 1.83 | 0.228 | 0.966 | 99.80 | 117.57 |
| 2 | 8.65 | 80.84 | 9.34 | 7.75 | 2.07 | 0.278 | 0.985 | 99.51 | 119.09 |
| 3 | 7.13 | 81.56 | 11.43 | 5.64 | 1.36 | 0.212 | 0.987 | 98.93 | 115.80 |
| 4 | 7.20 | 84.22 | 11.70 | 2.79 | 1.30 | 0.127 | 0.998 | 95.26 | 93.73 |
| 5 | 3.29 | 43.13 | 13.10 | 12.44 | 31.34 | 0.116 | 0.997 | 97.04 | 97.50 |
| 6 | 7.24 | 82.16 | 11.34 | 4.90 | 1.59 | 0.306 | 0.974 | 99.69 | 71.95 |
| 7 | 5.04 | 60.87 | 12.07 | 27.06 | 0.00 | 0.070 | 0.930 | 89.03 | 78.62 |
| 8 | 7.29 | 82.09 | 11.26 | 5.03 | 1.62 | 0.389 | 0.994 | 99.68 | 95.10 |

[1]t-3,5DFNB = trans - 2,3-Bis[bis(3-fluorophenyl)phosphinomethyl]norbornane
[2]Catalyst = Rh(CO)$_2$ Acetylacetonate

TABLE III

1-Hexene Hydroformylation Results using Norbornane Ligand t-pCF3NB[1]

| Run | Catalyst[2] (mmoles) | Ligand (mmoles) | Rxr Temp. (°C.) | Rxr Press. (psig) | Initial H$_2$/CO Ratio | Product 1-Hexene grams | Product wt. % 1-Hexene | Product wt. % Heptanal | Product wt. % 2Mehexal | Product wt. % 2-Hexene | Product wt. % Hexane |
|---|---|---|---|---|---|---|---|---|---|---|---|
| 1 | (0.105) | (0.42) | 110 | 150 | 2:1 | 13.77 | 0.01 | 18.62 | 2.59 | 0.68 | 0.27 |
| 2 | (0.058) | (0.20) | 110 | 105 | 2:1 | 13.81 | 0.14 | 19.05 | 2.47 | 0.97 | 0.34 |
| 3 | (0.050) | (0.20) | 100 | 105 | 2:1 | 13.71 | 0.25 | 18.46 | 2.54 | 0.52 | 0.22 |
| 4 | (0.050) | (0.20) | 120 | 105 | 2:1 | 13.64 | 0.03 | 17.65 | 2.26 | 1.51 | 0.50 |
| 5 | (0.050) | (0.20) | 110 | 150 | 2:1 | 13.42 | 0.15 | 18.13 | 2.58 | 0.55 | 0.26 |
| 6 | (0.050) | (0.20) | 120 | 150 | 1:1 | 14.00 | 0.05 | 18.82 | 2.91 | 0.63 | 0.25 |
| 7 | (0.058) | (0.21) | 130 | 150 | 1:1 | 13.22 | 0.02 | 16.60 | 2.59 | 0.93 | 0.30 |
| 8 | Rh4(CO)12 (0.040) | (0.15) | 110 | 150 | 2:1 | 13.92 | 0.29 | 18.67 | 2.70 | 0.69 | 0.20 |
| 9 | Rh4(CO)12 (0.058) | (0.11) | 110 | 150 | 2:1 | 13.96 | 1.12 | 14.57 | 2.59 | 0.55 | 0.29 |

| Run | Linear/ Branch Ratio | Percent Select Heptal | Percent Select Br-Prod. | Percent Select 2-Hexene | Percent Select Hexane | Rate Constant (mins.-1/nM Rh) | R value | Percent Hexene Conv. | Percent Mass Acc. |
|---|---|---|---|---|---|---|---|---|---|
| 1 | 7.19 | 82.79 | 11.52 | 4.10 | 1.59 | 0.214 | 0.962 | 99.94 | 100.29 |
| 2 | 7.71 | 81.80 | 10.61 | 5.65 | 1.94 | 0.262 | 0.996 | 99.19 | 99.25 |
| 3 | 7.27 | 83.92 | 11.55 | 3.21 | 1.33 | 0.192 | 0.999 | 98.48 | 99.88 |
| 4 | 7.81 | 78.02 | 9.99 | 9.06 | 2.93 | 0.448 | 0.991 | 99.42 | 95.72 |
| 5 | 7.03 | 83.16 | 11.83 | 3.42 | 1.58 | 0.317 | 0.991 | 99.07 | 98.27 |
| 6 | 6.47 | 82.12 | 12.70 | 3.73 | 1.45 | 0.347 | 0.994 | 99.70 | 99.62 |
| 7 | 6.41 | 79.62 | 12.42 | 6.05 | 1.91 | 0.512 | 0.997 | 99.17 | 94.54 |
| 8 | 6.91 | 82.71 | 11.96 | 4.15 | 1.17 | 0.270 | 0.999 | 98.29 | 100.58 |
| 9 | 5.63 | 69.36 | 12.33 | 16.48 | 1.83 | 0.144 | 0.959 | 93.25 | 96.62 |

[1]t-pCF3NB = trans - 2,3-Bis[bis(3-fluorophenyl)phosphinomethyl]norbornane
[2]Catalyst = Rh(CO)$_2$ Acetylacetonate

TABLE IV

1-Hexene Hydroformylation Results using Norbornane Ligand t-2,5DFNB[1]

| Run | Catalyst[2] (mmoles) | Ligand (mmoles) | Rxr Temp. (°C.) | Rxr Press. (psig) | H$_2$/CO Ratio | Initial 1-Hexene grams | Product wt. % 1-Hexene | Product wt. % Heptanal | Product wt. % 2Mehexal | Product wt. % 2-Hexene | Product wt. % Hexane |
|---|---|---|---|---|---|---|---|---|---|---|---|
| 1 | (0.050) Rh(CO)2AcAc | (0.20) | 110 | 150 | 2:1 | 13.86 | 8.62 | 2.64 | 0.76 | 6.21 | 0.00 |
| 2 | (0.11) H(CO)Rh(Ph P)3 | (0.43) | 110 | 150 | 1:1 | 13.64 | 1.93 | 15.86 | 2.62 | 0.82 | 0.19 |
| 3 | (0.11) H(CO)Rh(Ph P)3 | (0.43) | 110 | 150 | 1:1 | 13.91 | 3.27 | 15.89 | 2.58 | 0.82 | 0.20 |
| 4 | (0.11) Rh(CO)2AcAc | (0.41) | 110 | 150 | 2:1 | 13.73 | 8.83 | 2.90 | 0.88 | 3.47 | 0.00 |
| 5 | (0.11) Rh(CO)2AcAc | (0.41) | 110 | 150 | 2:1 | 13.75 | 3.34 | 12.86 | 2.21 | 1.91 | 0.24 |
| 6 | (0.11) Rh(CO)2AcAc | (0.41) | 110 | 150 | 2:1 | 13.56 | 2.35 | 13.38 | 2.08 | 1.15 | 0.24 |
| 7 | (0.11) Rh4(CO)12 | (0.42) | 110 | 150 | 2:1 | 13.70 | 1.25 | 20.10 | 2.79 | 0.95 | 0.31 |
| 8 | (0.11) | (0.41) | 110 | 150 | 2:1 | 13.52 | 3.09 | 13.37 | 2.2 | 1.94 | 0.29 |

TABLE IV-continued

1-Hexene Hydroformylation Results using Norbornane Ligand t-2,5DFNB[1]

| Run | Catalyst (mmoles) | Ligand (mmoles) | Rxr Temp. (°C.) | Rxr Press. (psig) | $H_2$/CO Ratio | Initial 1-Hexene grams | Product wt. % 1-Hexene | Product wt. % Heptanal | Product wt. % 2Mehexal | Product wt. % 2-Hexene | Product wt. % Hexane |
|---|---|---|---|---|---|---|---|---|---|---|---|
| 9  | Rh(CO)2AcAc (0.105) | (0.42) | 130 | 105 | 2:1 | 13.98 | 9.03 | 4.69 | 0.77 | 1.52 | 0.35 |
| 10 | Rh(CO)2AcAc (0.112) | (0.45) | 130 | 150 | 2:1 | 14.04 | 4.84 | 12.48 | 1.89 | 1.60 | 0.39 |
| 11 | Rh(CO)12 (0.112) | (0.45) | 110 | 150 | 2:1 | 13.90 | 2.09 | 16.24 | 2.27 | 0.81 | 0.28 |

| Run | Linear/ Branch Ratio | Percent Select Heptal | Percent Select Br-Prod. | Percent Select 2-Hexene | Percent Select Hexane | Rate Constant (mins.-1/nM Rh) | R value | Percent Hexene Conv. | Percent Mass Acc. |
|---|---|---|---|---|---|---|---|---|---|
| 1  | 3.47 | 22.32 | 6.43  | 71.25 | 0.00 | —     | —     | 50.27 | 95.56  |
| 2  | 6.05 | 79.92 | 13.20 | 5.61  | 1.27 | 0.011 | 0.968 | 88.34 | 92.71  |
| 3  | 6.16 | 80.06 | 13.00 | 5.61  | 1.34 | 0.009 | 0.988 | 81.73 | 98.29  |
| 4  | 3.30 | 34.16 | 10.37 | 55.47 | 0.00 | —     | —     | 41.47 | 83.94  |
| 5  | 5.82 | 71.52 | 12.29 | 14.42 | 1.77 | —     | —     | 79.87 | 92.17  |
| 6  | 6.43 | 77.17 | 12.00 | 9.00  | 1.83 | 0.011 | 0.983 | 84.46 | 85.22  |
| 7  | 7.20 | 81.74 | 11.35 | 5.24  | 1.67 | 0.020 | 0.985 | 93.55 | 108.81 |
| 8  | 6.08 | 71.93 | 11.84 | 14.16 | 2.07 | 0.015 | 0.973 | 81.59 | 94.86  |
| 9  | 6.09 | 58.72 | 9.64  | 25.83 | 5.81 | —     | —     | 39.46 | 83.06  |
| 10 | 6.60 | 73.16 | 11.08 | 12.73 | 3.03 | 0.009 | 0.985 | 72.20 | 101.68 |
| 11 | 7.15 | 81.28 | 11.36 | 5.50  | 1.86 | 0.015 | 0.942 | 87.57 | 101.38 |

[1]t-2,5DFNB = trans - 2,3-Bis[bis(2,5-fluorophenyl)phosphinomethyl]norbornane
[2]Catalyst = Rh(CO)$_2$ Acetylacetonate

TABLE V

1-Hexene Hydroformylation Results using Aromatic Ligand[1]

| Run | Catalyst (mmoles) | Ligand (mmoles) | Rxr Temp. (°C.) | Rxr Press. (psig) | $H_2$/CO Ratio | Initial 1-Hexene grams | Product wt. % 1-Hexene | Product wt. % Heptanal | Product wt. % 2Mehexal | Product wt. % 2-Hexene | Product wt. % Hexane |
|---|---|---|---|---|---|---|---|---|---|---|---|
| 1 | (0.10) | (0.32) | 110 | 150 | 2:1 | 13.35 | 3.33 | 15.07 | 0.39 | 1.53 | 0.37 |
| 2 | (0.10) | (0.16) | 110 | 150 | 2:1 | 13.24 | 0.08 | 18.31 | 0.91 | 3.36 | 0.55 |

| Run | Linear/ Branch Ratio | Percent Select Heptal | Percent Select Br-Prod. | Percent Select 2-Hexene | Percent Select Hexane | Rate Constant (mins.-1/nM Rh) | R value | Percent Hexene Conv. | Percent Mass Acc. |
|---|---|---|---|---|---|---|---|---|---|
| 1 | 38.64 | 83.60 | 2.16 | 11.52 | 2.72 | 0.010 | 0.995 | 79.96 | 104.18 |
| 2 | 20.12 | 74.71 | 1.71 | 18.61 | 2.97 | 0.036 | 0.994 | 99.56 | 114.44 |

[1]1,2-Bis[bis(3,5-difluorophenyl)phosphino]-5-fluorobenzene

What is claimed is:

1. The compound bis(3,5-difluorophenyl)-phosphine oxide.

2. The compound bis(3,5-difluorophenyl)-phosphinous acid.

3. The compound of claim 2 is crystalline form.

* * * * *